(12) United States Patent
Gerlach

(10) Patent No.: US 12,291,532 B2
(45) Date of Patent: May 6, 2025

(54) SUBSTITUTED XANTHINES AS MODULATORS OF TRPC5 ACTIVITY

(71) Applicants: Boehringer Ingelheim International GmbH, Ingelheim am Rhein (DE); Hydra Biosciences, LLC, Belmont, MA (US)

(72) Inventor: Kai Gerlach, Ingelheim am Rhein (DE)

(73) Assignees: Boehringer Ingelheim International GmbH, Ingelheim Am Rhein (DE); Hydra Biosciences, LLC, Belmont, MA (US)

( * ) Notice: Subject to any disclaimer, the term of this patent is extended or adjusted under 35 U.S.C. 154(b) by 907 days.

(21) Appl. No.: 17/312,831

(22) PCT Filed: Dec. 10, 2019

(86) PCT No.: PCT/EP2019/084373
§ 371 (c)(1),
(2) Date: Jun. 10, 2021

(87) PCT Pub. No.: WO2020/120449
PCT Pub. Date: Jun. 18, 2020

(65) Prior Publication Data
US 2022/0056032 A1 Feb. 24, 2022

(30) Foreign Application Priority Data
Dec. 12, 2018 (EP) ..................................... 18212059

(51) Int. Cl.
*A61K 31/519* (2006.01)
*C07D 473/06* (2006.01)
*C07D 487/04* (2006.01)

(52) U.S. Cl.
CPC .................. *C07D 473/06* (2013.01)

(58) Field of Classification Search
CPC .......................... A61K 31/519; C07D 487/04
USPC ........................................ 514/262.1; 544/262
See application file for complete search history.

(56) References Cited

FOREIGN PATENT DOCUMENTS

| | | |
|---|---|---|
| CN | 105143229 A | 12/2015 |
| JP | 2016-513717 A | 5/2016 |
| JP | 2017-523229 A | 8/2017 |
| WO | WO 2014/143799 A2 | 9/2014 |
| WO | WO 2018/146485 A1 | 8/2018 |
| WO | WO 2019/011802 A1 | 1/2019 |
| WO | WO-2020120449 A1 * | 6/2020 ............. A61P 25/16 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion for PCT/EP2019/084373 mailed Feb. 4, 2020.
International Preliminary Report on Patentability for PCT/EP2019/084373 mailed Jun. 24, 2021.
PCT/EP2019/084373, Feb. 4, 2020, International Search Report and Written Opinion.
PCT/EP2019/084373, Jun. 24, 2021, International Preliminary Report on Patentability.

* cited by examiner

*Primary Examiner* — Douglas M Willis
(74) *Attorney, Agent, or Firm* — Wolf, Greenfield & Sacks, P.C.

(57) ABSTRACT

The present invention relates to compounds of formula (I) a process for their manufacture, pharmaceutical compositions containing them and their use in therapy, particularly in the treatment of conditions having an association with TRPC5 containing ion channels. $R^1$, $R^2$, $R^3$, $R^4$ and $R^5$ have meanings given in the description.

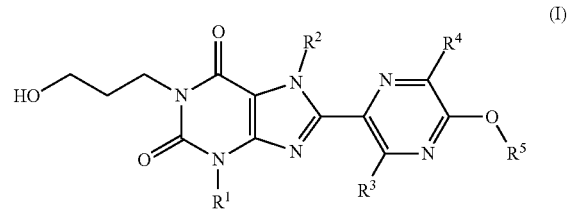

25 Claims, No Drawings

SUBSTITUTED XANTHINES AS MODULATORS OF TRPC5 ACTIVITY

CROSS REFERENCE TO RELATED APPLICATION(S)

This Application is a National Stage filing under 35 U.S.C. 0 371 of International Patent Application No. PCT/EP2019/084373, filed Dec. 10, 2019, which claims priority to European Application No. 18212059.2, filed Dec. 12, 2019, the entire contents of which are incorporated herein by reference.

FIELD OF THE INVENTION

The present invention relates to substituted xanthine derivatives, pharmaceutical compositions containing them and their use in therapy, particularly in the treatment or prevention of conditions having an association with TRPC5 containing ion channels.

BACKGROUND OF THE INVENTION

A variety of ion channel proteins exist to mediate ion flux across cellular membranes. The proper expression and function of ion channel proteins is essential for the maintenance of cell function, and the intracellular communication. Numerous diseases are the result of mis-regulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

Cation channels such as the transient receptor potential (TRP) cation channel subfamily C, member 5 (TRPC5) modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Homomeric TRPC5 ion channels are signal transduction gated, Ca2+-permeable channels predominantly expressed in neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g. TRPC5-TPRC1 or TRPC5-TRPC4 heteromultimer). Examples of TRPC5 in the literature include the following: Nature 2008 Jan. 3; 451 (7174):69-72; Mol Pharmacol. 2008 January; 73 (1):42-9; J Biol Chem. 2007 Nov. 16; 282 (46):33868-78; Biochem Biophys Res Commun. 2008 Jan. 11; 365 (2):239-45; J Biol Chem. 2006 Nov. 3; 281 (44): 33487-96; Eur J Pharmacol. 2005 Mar. 14; 510 (3):217-22; J Biol Chem. 2006 Feb. 24; 281 (8):4977-82; Biochem Soc Trans. 2007 February; 35 (Pt. 1):101-4; Handb Exp Pharmacol. 2007; (179):109-23; J Biol Chem. 2005 Mar. 25; 280 (12):10997-1006; J Physiol. 2006 Jan. 15; 570 (Pt 2):219-35; and Nat Neurosci. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Compounds inhibiting TRPC5 containing ion channels are for example useful for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e. TRPC5-TRPC1 and TRPC1-TRPC3-TRPC5). WO 2014/143799 discloses xanthine derivatives that inhibit TRPC5. They modulate the function of TRPC5 by inhibiting a TRPC5-mediated ion flux or by inhibiting the inward current, the outward current, or both currents mediated by TRPC5.

DETAILED DESCRIPTION OF THE INVENTION

The present invention provides novel substituted xanthine derivatives of formula I

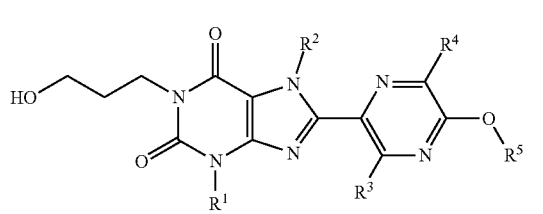

in which
$R^1$ represents ethyl, isopropyl, isobutyl, cyclobutyl;
$R^2$ represents

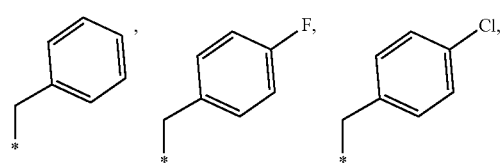

3
-continued

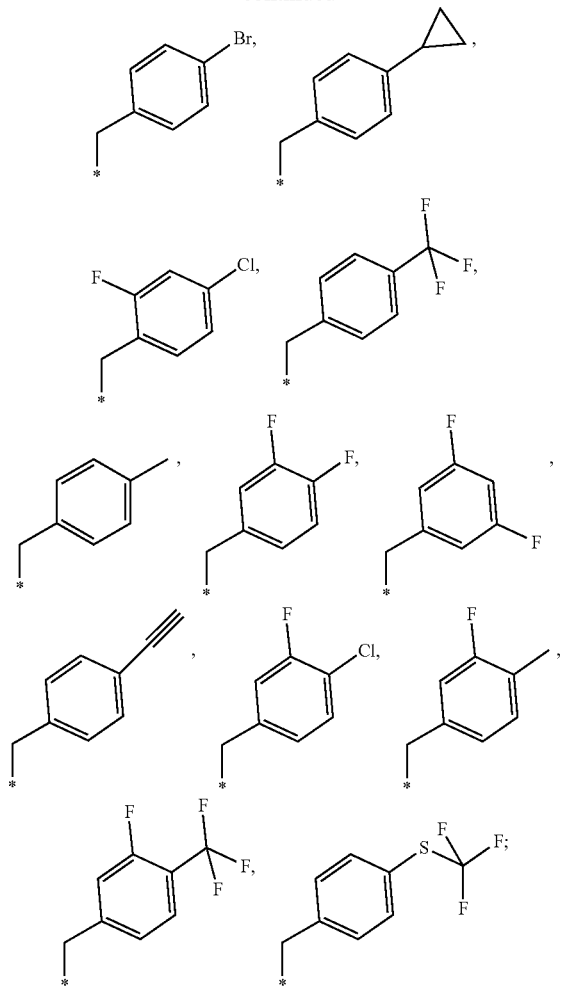

$R^3$ represents hydrogen, fluoro, $C_1$-$C_3$-alkyl optionally substituted with one or more fluorine atoms;
$R^4$ represents hydrogen or fluoro;
$R^5$ represents

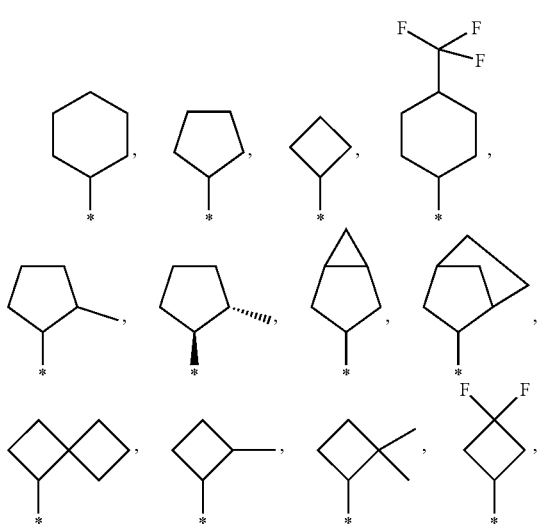

4
-continued

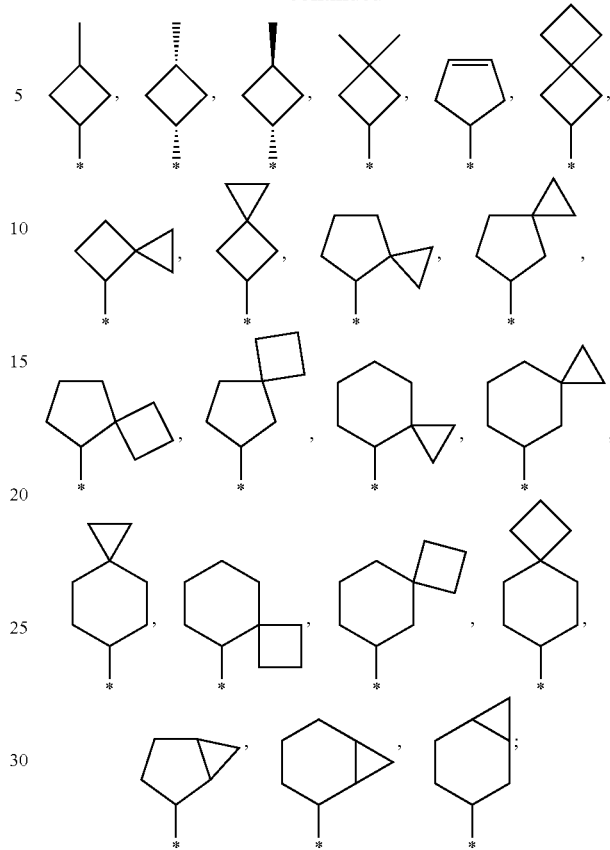

which groups
  are optionally substituted with one or more fluorine atoms and/or one or more $C_1$-$C_3$-alkyl fluorinated with one or more fluorine atoms;
or a physiologically acceptable salt thereof.
In another embodiment, in the general formula I,
$R^1$ represents ethyl, isopropyl;
$R^2$ represents

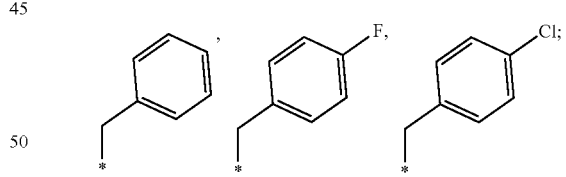

$R^3$ represents hydrogen, methyl;
$R^4$ represents hydrogen;
$R^5$ represents

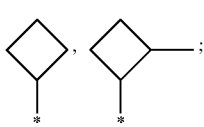

or a physiologically acceptable salt thereof.
Compounds of the present invention are potent TRPC5-inhibitors. They differ from the structurally closest compounds disclosed in WO 2014/143799 in that the C8-position of the xanthine in the compounds of the present invention is substituted with a 2-pyrazinyl group rather than with a phenyl group.

The compounds of the present invention modulate the function of TRPC5 by inhibiting a TRPC5-mediated ion flux or by inhibiting the inward current, the outward current, or both currents mediated by TRPC5. They are characterized by a higher potency for inhibition of TRPC5, when compared to the closest prior art compounds in WO 2014/143799.

The present invention thus provides compounds for use in the treatment of a TRPC5 mediated disorder.

The present invention further provides methods of treating a TRPC5 mediated disorder in a human subject comprising administering to the subject a compound or composition of a compound of the present invention or a pharmaceutically acceptable salt thereof.

In one aspect, the invention relates to a method for treating a condition for which reduced TRPC5 activity can reduce the severity of the condition, by administering a TRPC5 antagonist, such as a compound as described herein that inhibits a TRPC5-mediated current and/or a TRPC5-mediated ion flux. Described herein are compounds, which are TRPC5 antagonists that have a measured 1050 for inhibition of TRPC5 of 5 nanomolar or less. In certain embodiments, the compounds described herein, which are TRPC5 antagonists inhibit one or both of inward and outward TRPC5-mediated currents with an 1050 of 5 nanomolar or less. In certain embodiments, the compounds described herein inhibit at least 95% of a TRPC5-mediated current or a TRPC5-mediated ion flux when administered at 1 micromolar or less.

In another aspect, the compounds described herein, which are TRPC5 antagonists can be used to inhibit a function of TRPC5, for example a TRPC5-mediated current and/or a TRPC5-mediated ion flux. In some embodiments, the compounds described herein can be used to inhibit a TRPC5 mediated current in vitro, for example in cells in culture. In other embodiments, the compounds described herein can be used to inhibit a TRPC5 mediated current in vivo. In certain embodiments, the compounds described herein inhibit both an inward and an outward TRPC5-mediated current.

Definitions

Terms not specifically defined herein should be given the meanings that would be given to them by one skilled in the art in light of the disclosure and the context.

The terms "antagonist" and "inhibitor" are used interchangeably to refer to an agent that decreases or suppresses a biological activity, such as to repress an activity of an ion channel, such as TRPC5. TRPC5 ion channels as described herein include homomultimeric and heteromultimeric structures (e.g. homomultimeric TRPC5 and heteromeric TRPC5-TRPC1 or TRPC5-TRPC4). TRPC5 antagonists include inhibitors having any combination of the structural and/or functional properties disclosed herein.

An "effective amount" of, e.g. a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention includes an amount of a TRPC5 antagonist effective to decrease one or more in vitro or in vivo function of a TRPC5 channel. Exemplary functions include, but are not limited to, membrane polarization (e.g. an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or an amount sufficient to inhibit TRPC5 mediated ion flux.

The TRPC5 antagonists for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The terms "compound" and "agent" are used interchangeably to refer to the inhibitors/antagonists of the invention.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S- and R-forms, or diastereomerically pure forms), 2-phenylglycinol, norephedrine, ephedrine, N-methylephedrine, cyclohexylethylamine, and 1,2-diaminocyclohexane.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Unless specifically indicated, throughout the specification and the appended claims, a given chemical formula or name shall encompass tautomers and all stereo, optical and geometrical isomers (e.g. enantiomers, diastereoisomers, E/Z isomers) and racemates thereof, as well as mixtures in different proportions of the separate enantiomers, mixtures of diastereoisomers, or mixtures of any of the foregoing forms where such isomers and enantiomers exist.

Compounds of the invention can also include all isotopes of atoms occurring in the intermediates or final compounds. For example, the compound of the invention may be radiolabeled with radioactive isotopes, such as for example tritium ($^3$H) or carbon-14 ($^{14}$C). All isotopic variations, whether radioactive or not, are intended to be encompassed within the scope of the present invention.

As used herein, "pharmaceutically acceptable salts" refer to derivatives of the disclosed compounds wherein the parent compound forms a salt with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid. Also included are the salts of amino acids such as arginate, and salts of organic acids like glucuronic or galactunoric acids (see, for example, Berge et al., "Pharmaceutical Salts", Journal of Pharmaceutical Science, 1977, 66, 1-19).

Examples for cations and bases forming a pharmaceutically acceptable salt with a parent compound containing an acidic moiety include Na$^+$, K$^+$, Ca$^{2+}$, Mg$^{2+}$, NH$_{4+}$, L-arginine, 2,2'-iminobisethanol, L-lysine, N-methyl-D-glucamine or tris(hydroxymethyl)-aminomethane.

The neutral form of the compounds of the invention is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The terms "TRPC5", "TRPC5 protein", and "TRPC5 channel" are used interchangeably throughout the application. Unless expressly stated, the term TRPC5 includes homomultimeric structures (e.g. homomultimeric TRPC5) and heteromultimeric structures (e.g. heteromultimeric TRPC5-TRPC1).

Biological Assays

The biological activity of compounds is determined by the following methods:

Assay A: Determination of TRPC5-Inhibition

Patch clamp experiments permit the detection of currents through the TRPC5 channel in a cell line. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 μM free Ca2+ in the pipette (intracellular) solution, and 80 μM LaCl$_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM CaCl$_2$, 2.27 mM MgCl$_2$ and 10 mM HEPES, pH 7.2, with 1,400 nM calculated free Ca2+. The external solution consisted of 150 mM NaCl, 4.5 mM 15 KCl, 1 mM MgCl$_2$, 2 mM CaCl$_2$, 10 mM HEPES, 10 mM glucose, 1 mM EGTA, pH 7.4. Upon addition of LaCl$_3$, TRPC5 current was induced only in TRPC5-expressing cells and not in parental HEK293 TREx cells. Removal of the LaCh stimulus causes most of the current to go away. Potential blockers were tested for ability to block both inward and outward currents in the continued presence of LaCl$_3$.

IC50 of a compound of the invention was estimated by testing the compound 500 nM. When 500 nM of a compound showed no block, 1050 was estimated as >1 μM. Compounds blocking 50% or more at 500 nM are retested at multiple concentrations, and the % block is fitted by standard equations to determine 1050 accurately, using a ⅚ point concentration-response experiment.

Biological Data

TABLE 1

In vitro potencies of the closest prior art compounds of WO2014/143799 determined in the Assay A (described above)

| Example | Structure | Assay A TRPC5 inhibition |
|---|---|---|
| Example 441 in WO2014/143799 | 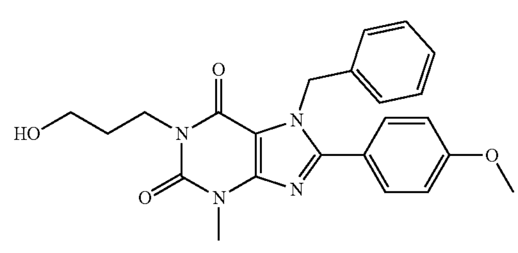 [SMILES: COc1ccc(-c2nc3c(c(=O)n(CCCO)c(=O)n3C)n2Cc2ccccc2)cc1] | 324 nM |

TABLE 1-continued

Example 465 in WO2014/143799 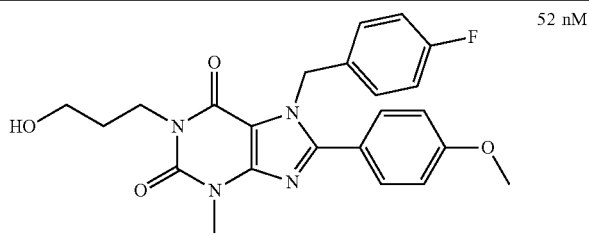 52 nM

Compounds of the present invention surprisingly show a much higher potency in TRPC5-inhibition when measured in the same assay (Assay A) than the closest prior art compounds (examples #441 and #465 in WO2014/143799).

The compounds of the present invention differ structurally from Examples 441 and 465 in WO 2014/143799, i.e. the closest prior art compounds, in that the C8-position of the xanthine in the presently claimed compounds is substituted with a 2-pyrazinyl rather than with a phenyl group as in Examples 441 and 465 of WO 2014/143799. Furthermore, the heteroaryl group in the presently claimed compounds is substituted with a cycloalkyl-O— group rather than with a methoxy-group, as in Examples 441 and 465 of WO 2014/143799. These structural differences unexpectedly result in a markedly increased potency in TRPC5-inhibition. (Tables 1 and 2).

These results demonstrate that compounds of the present invention unexpectedly are superior to the structurally most similar example disclosed in WO2014/143799 (closest prior art compounds) in TRPC5 inhibition. Consequently, compounds of the present invention are more viable for human use.

Table 2: In vitro potencies of compounds of the present invention determined in Assay A (described above)

| Example | Structure | Assay A TRPC5 inhibition |
|---|---|---|
| 1 | 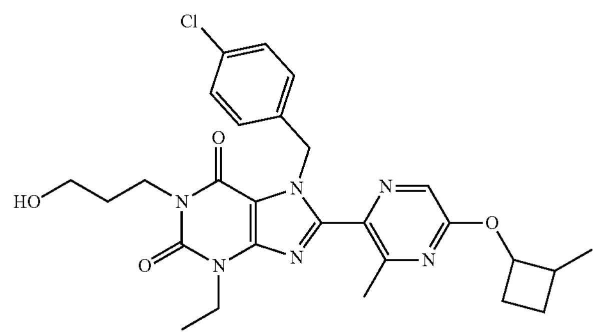 [SMILES: CCn1c(=O)n(CCCO)c(=O)c2c1nc(-c1ncc(OC3CCC3C)nc1C)n2Cc1ccc(Cl)cc1] | 0.172 nM |
| 2 | 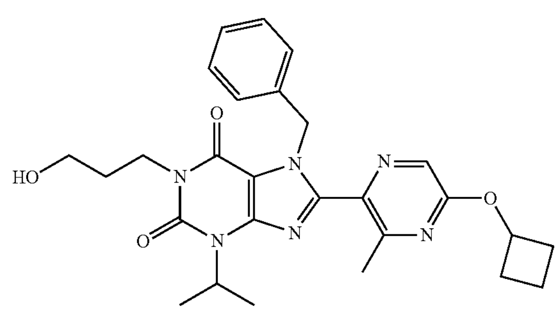 [SMILES: Cc1nc(OC2CCC2)cnc1-c1nc2c(c(=O)n(CCCO)c(=O)n2C(C)C)n1Cc1ccccc1] | 0.207 nM |
| 3 | 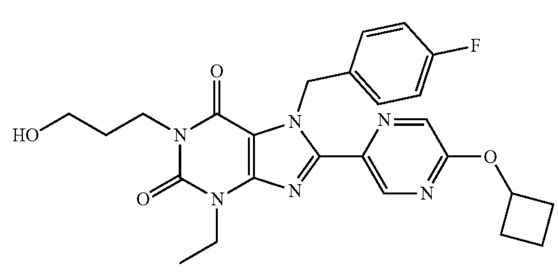 [SMILES: CCn1c(=O)n(CCCO)c(=O)c2c1nc(-c1cnc(OC3CCC3)cn1)n2Cc1ccc(F)cc1] | 0.506 nM |

| Example | Structure | Assay A TRPC5 inhibition |
|---|---|---|
| 4 | 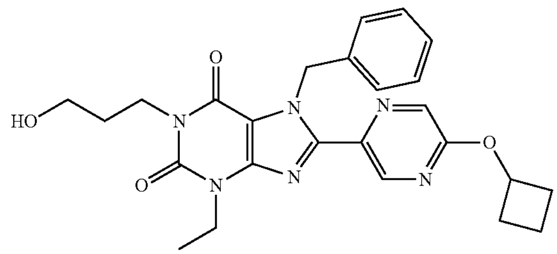 [SMILES: CCn1c(=O)n(CCCO)c(=O)c2c1nc(-c1cnc(OC3CCC3)cn1)n2Cc1ccccc1] | 1.114 nM |
| 5 | 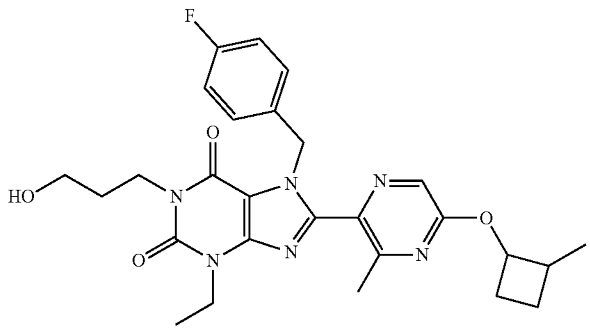 [SMILES: CCn1c(=O)n(CCCO)c(=O)c2c1nc(-c1ncc(OC3CCC3C)nc1C)n2Cc1ccc(F)cc1] | 0.290 nM |
| 6 | 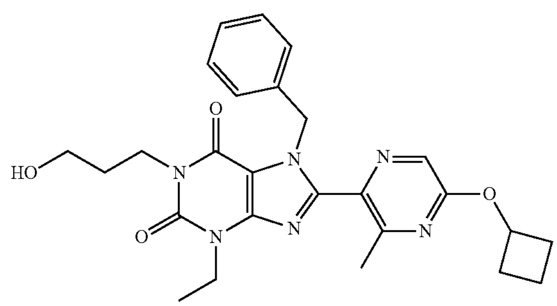 [SMILES: CCn1c(=O)n(CCCO)c(=O)c2c1nc(-c1ncc(OC3CCC3)nc1C)n2Cc1ccccc1] | 1.219 nM |

Use in Treatment/Method of Use

The present invention is directed to compounds which are useful in the treatment of a disease, disorder and condition wherein the inhibition of the activity of the transient receptor potential cation channel TRPC5 is of therapeutic benefit. This includes but is not limited to the treatment and/or prevention of psychiatric, neurological or neurodegenerative conditions, pain, seizure, non-neuronal conditions, and cancer.

Psychiatric conditions include diseases associated with dysregulated emotional processing (e.g. borderline personality disorder or depressive disorders like major depression, major depressive disorder, psychiatric depression, dysthymia, and postpartum depression, and bipolar disorders), anxiety and fear-related disorders (e.g. post-traumatic stress disorder, panic disorder, agoraphobia, social phobias, generalized anxiety disorder, panic disorder, social anxiety disorder, obsessive compulsive disorder, and separation anxiety), memory disorders (e.g. Alzheimer's disease, amnesia, aphasia, brain injury, brain tumor, chronic fatigue syndrome, Creutzfeldt-Jakob disease, dissociative amnesia, fugue amnesia, Huntington's disease, learning disorders, sleeping disorders, multiple personality disorder, pain, post-traumatic stress disorder, schizophrenia, sports injuries, stroke, and Wernicke-Korsakoff syndrome), disorders associated with impaired impulse control and addiction.

Neurological or neurodegenerative conditions include e.g. Alzheimer's disease (AD), Parkinson's disease, Huntington's disease, amyotrophic lateral sclerosis (ALS), and other brain disorders caused by trauma or other insults including aging.

Pain disorders include nociceptive pain, inflammatory pain, cancer pain, and neuropathic pain (e.g. cancer pain, osteoarthritic pain, rheumatoid arthritis pain, post-herpetic neuralgia, pain due to burns, and other indications). The pain can be chronic or acute.

Seizures may be induced by excitotoxicity of a variety of origins. Commonly excess neuronal firing can drive seizure activity. Compounds that reduce the hyperexcitability of relevant neuronal populations have significant potential in reducing seizure activity. Compounds of the invention that inhibit TRPC5 may reduce hyperexcitability and thus reduce seizure activity.

Non-neuronal conditions include nephropathy, proteinuric kidney disease, liver diseases such as hepatic dyslipidemia associated with cholestasis, non-alcoholic steatohepatitis (NASH), non-alcoholic fatty liver disease (NAFLD) [WO2018/146485], itch, disorders associated with malfunction of the cardiovascular-vascular system or vascular permeability (e.g. pulmonary arterial hypertension, acute respiratory distress syndrome (ARDS), maladaptive cardiac remodeling, disorders associated with maladaptive blood pressure control like hypertension or hypotension, and other medical conditions such as diabetes, insulin resistance, metabolic syndrome and obesity. It is envisaged that the use for treatment of non-neuronal conditions may also extend to the use for cosmetic weight loss (WO2018/146485).

Another aspect of the invention relates to pharmaceutical compositions for use in a human patient, comprising an effective amount of a compound described herein (or a pharmaceutically acceptable salt thereof), and one or more pharmaceutically acceptable excipient(s). The invention further contemplates the use of the compounds described herein in the manufacture of a medicament or a pharmaceutical composition to treat or reduce the symptoms of any of the diseases or conditions provided in the specification. The compounds described herein can be used for treating a particular disease or condition and can be formulated for administration via a route appropriate for the particular disease or condition.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable compositions for administering the compounds of the present invention will be apparent to those with ordinary skill in the art and include for example tablets, pills, capsules, suppositories, lozenges, troches, solutions, syrups, elixirs, sachets, injectables, inhalatives, and powders. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and compressing the resulting mixture to tablets.

Combination Therapy

The compounds of the present invention can be used alone or in combination with other active pharmaceutical ingredients. In particular, compounds according to the present invention can be combined with other treatment options known to be used in the art in connection with a treatment of any of the indications the treatment of which is in the focus of the present invention.

Among such active pharmaceutical ingredients or treatment options that are considered suitable for combination with the compounds and the treatment according to the present invention are antidepressants, mood stabilizers, typical and atypical antipsychotics, anxiolytics, antiepileptic drugs, sleeping agents, cognitive enhancers, stimulants, additional psychoactive drugs, anti-inflammatory drugs, analgesic drugs, chemotherapeutic drugs as well as active pharmaceutical ingredients used or potentially useful in the treatment of metabolic disorders, liver diseases and kidney diseases, the latter active pharmaceutical ingredients also including potential inhibitors of TRPC3 and/or TRPC6.

EXPERIMENTAL SECTION

List of abbreviations:

| | |
|---|---|
| ACN | acetonitrile |
| conc | concentrated |
| d | day(s) |
| DCM | dichloromethane |
| DIPEA | N-ethyl-diisopropylamine |
| DMAP | 4-dimethylaminopyridine |
| DMF | N,N-dimethylformamide |
| DMSO | dimethylsulfoxide |
| EtOAc | ethyl acetate |
| g | gram |
| h | hour(s) |
| HOAc | acetic acid |
| HPLC | high performance liquid chromatography |
| MeOH | Methanol |
| min | minute(s) |
| mg | milligram |
| mL | milliliter |
| N | normal |
| rt | room temperature |
| RT | retention time |
| SFC | supercritical fluid chromatography |
| THF | tetrahydrofuran |
| TFA | trifluoracetic acid |
| µL | microliter |

HPLC-Methods:

Method Name: A
Column: XBridge BEH C18_2.1 × 30 mm, 1.7 µm
Column Supplier: Waters

| Gradient/ Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: B
Column: XBridge BEH Phenyl, 2.1 × 30 mm, 1.7 μm
Column Supplier: Waters

| Gradient/ Solvent Time [min] | % Sol [H$_2$O, 0.1% NH$_3$] | % Sol [Acetonitril] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: C
Column: XBridge C18, 4.6 × 30 mm, 3.5 μm
Column Supplier: Waters

| Gradient/ Solvent Time [min] | % Sol [H$_2$O, 0.1% NH$_3$] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: D
Column: XBridge BEH C18, 2.1 × 30 mm, 1.7 μm
Column Supplier: Waters

| Gradient/ Solvent Time [min] | % Sol [H$_2$O, 0.1% NH$_3$] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| Method Name: | E |
| Column: | XBridge BEH C18_2.1 × 30 mm_2.5 μm |
| Column Supplier: | Waters |

| Gradient/<br>Solvent<br>Time [min] | % Sol<br>[H$_2$O,<br>0.1% NH$_3$] | % Sol<br>[ACN] | Flow<br>[mL/min] | Temp<br>[° C.] |
|---|---|---|---|---|
| 0.00 | 50 | 50 | 1.3 | 60 |
| 0.02 | 50 | 50 | 1.3 | 60 |
| 1.00 | 0 | 100 | 1.3 | 60 |
| 1.10 | 0 | 100 | 1.3 | 60 |

| Method Name: | F |
| Column: | Sunfire C18_3.0 × 30 mm_2.5 μm |
| Column Supplier: | Waters |

| Gradient/<br>Solvent<br>Time [min] | % Sol<br>[H$_2$O, 0.1%<br>TFA (v/v)] | % Sol<br>[ACN] | Flow<br>[mL/min] | Temp<br>[° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |

| Method Name: | G |
| Column: | XBridge BEH C18_2.1 × 30 mm_2.5 μm |
| Column Supplier: | Waters |

| Gradient/<br>Solvent<br>Time [min] | % Sol<br>[H$_2$O,<br>0.1% NH$_3$] | % Sol<br>[ACN] | Flow<br>[mL/min] | Temp<br>[° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| Method Name: | H |
| Column: | XBridge BEH C18_2.1 × 30 mm_1.7 μm |
| Column Supplier: | Waters |

| Gradient/<br>Solvent<br>Time [min] | % Sol<br>[H$_2$O,<br>0.1% NH$_3$] | % Sol<br>[ACN] | Flow<br>[mL/min] | Temp<br>[° C.] |
|---|---|---|---|---|
| 0.00 | 50 | 50 | 1.3 | 60 |
| 0.02 | 50 | 50 | 1.3 | 60 |
| 1.00 | 0 | 100 | 1.3 | 60 |
| 1.10 | 0 | 100 | 1.3 | 60 |

| Method Name: | I |
| Column: | Lux ® Cellulose_3 4.6 × 250 mm_5 μm |
| Column Supplier: | Phenomenex |

| Gradient/<br>Solvent<br>Time [min] | % Sol<br>[scCO$_2$] | % Sol<br>[MEOH<br>20 mM<br>NH$_3$] | Flow<br>[mL/min] | Temp<br>[° C.] | Back<br>pressure<br>(PSI) |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

| | | Method Name: J | | | |
| | Column: Chiralpak ® IA_4.6 × 250 mm_5 μm | | | | |
| | Column Supplier: Daicel | | | | |

| Gradient/ Solvent Time [min] | % Sol [scCO$_2$] | % Sol [MEOH 20 mM NH$_3$] | Flow [mL/min] | Temp [° C.] | Back pressure (PSI) |
| --- | --- | --- | --- | --- | --- |
| 0.0 | 85.0 | 15.0 | 4.0 | 40.0 | 2175.0 |
| 10.0 | 85.0 | 15.0 | 4.0 | 40.0 | 2175.0 |

| | | Method Name: K | | | |
| | Column: Lux ® Amylose-2_4.6 × 250 mm_5 μm | | | | |
| | Column Supplier: Phenomenex | | | | |

| Gradient/ Solvent Time [min] | % Sol [scCO$_2$] | [MEOH 20 mM NH$_3$] | Flow [mL/min] | Temp [° C.] | Back pressure (PSI) |
| --- | --- | --- | --- | --- | --- |
| 0.0 | 95.0 | 5.0 | 4.0 | 40.0 | 2175.0 |
| 10.0 | 95.0 | 5.0 | 4.0 | 40.0 | 2175.0 |

NMR method: NMR spectra were recorded on a Bruker AVANCE IIIHD 400 MHz instrument using TopSpin 3.2 pl6 software. Chemical shifts are given in parts per million (ppm) downfield from internal reference trimethylsilane in δ units. Selected data are reported in the following manner: chemical shift (multiplicity, coupling constants (J), number of hydrogens). Abbreviations are as follows: s (singulet), d (doublet), t (triplet), q (quartet), spt (septet), m (multiplet), br (broad).

Intermediates:

Intermediate 1.1

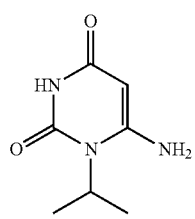

1.1

The reaction was performed under argon atmosphere and in dried glassware. Na (4.50 g, 196 mmol) was added in pieces to dry propan-2-ol (150 mL). The mixture was stirred 2 h and heated to 95° C. After the Na was completely dissolved, isopropyl-urea (10.0 g, 97.9 mmol) and cyanoacetic acid ethyl ester (10.4 mL, 97.9 mmol) were added and the mixture was stirred overnight at 95° C. The mixture was cooled down and H$_2$O (40.0 mL) was added and the pH was adjusted to 6 with conc HCl. Stirring was continues under ice cooling and N2 atmosphere for 12 h. The obtained precipitate was filtered and dried to obtain 7.33 g of the product.

MS (ESI$^+$): (M+H)$^+$ 170

HPLC: RT=0.23 min, Method F

Intermediate 1.2

1.2

The reaction was performed under argon atmosphere and in dried glassware. Na (20.9 g, 908 mmol) was added in pieces to dry ethanol (600 mL). The mixture was stirred 3 d and heated to 60° C. After the Na was completely dissolved, ethylurea (40.0 g, 454 mmol) and ethyl 2-cyanoacetate (48.3 mL, 454 mmol) were added and the mixture was stirred 4 d at reflux. The mixture was concentrated in vacuo, H$_2$O (200 mL) was added and the pH was adjusted to 7 with conc HCl. Stirring was continued under ice cooling for 30 min. The obtained precipitate was filtered, washed with H$_2$O and dried to obtain 48.59 g of the product.

MS (ESI$^+$): (M+H)+ 156

HPLC: RT=1.18 min, Method B

Intermediate 2.1

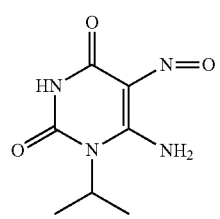

2.1

To a mixture of intermediate 1.1 (1.00 g, 5.91 mmol) in HCl (1 mol/l, 16.5 mL, 16.5 mmol) NaNO$_2$ (571 mg, 8.28 mmol) in H$_2$O (6.00 mL) was added dropwise. NaOH (4 N, about 4 mL) was added until the pH of the solution reached pH=9. The obtained precipitate was filtered, washed with MeOH and tert-butylmethylether and dried to obtain 0.79 g of the product.

MS (ESI+): (M+H)+ 199
HPLC: RT=0.24 min, Method F

Intermediate 2.2

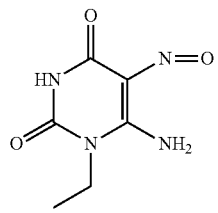

2.2

To a mixture of intermediate 1.2 (48.6 g, 0.304 mol) in HCl (1 mol/l, 800 mL, 800 mmol) NaNO$_2$ (29.3 g, 0.425 mol) in H$_2$O (280 mL) was added dropwise. The mixture was stirred overnight at rt. Then the mixture was basified with NaOH (60%, about 15 mL). The obtained precipitate was filtered, washed with MeOH and tert-butylmethylether and dried to obtain 43.8 g of the product.

MS (ESI+): (M+H)+ 185
HPLC: RT=0.09 min, Method B

Intermediate 3.1

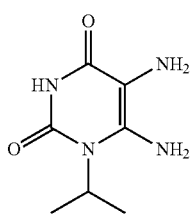

3.1

A mixture of intermediate 2.1 (8.04 g, 40.6 mmol), Pd/C (10%, 1.9 g), MeOH (120 mL), H$_2$O (80 mL) and HCl solution (4 mol/L, 11.2 mL, 44.6 mmol) was hydrogenated at rt and 50 psi of H$_2$ for 4 h. The mixture was filtered, MeOH was evaporated, ACN was added and freezedried to obtain 3.04 g of the product.

MS (ESI+): (M+H)+ 185
HPLC: RT=0.01 min, Method D

Intermediate 3.2

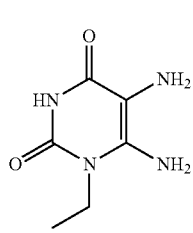

3.2

A mixture of intermediate 2.2 (43.3 g, 235 mmol), Pd/C (10%, 4.95 g), MeOH (400 mL), H$_2$O (300 mL) and HCl solution (1 mol/L, 259 mL, 259 mmol) was hydrogenated at rt and 50 psi of H$_2$ for 1 d. The mixture was filtered, MeOH was evaporated, ACN was added and freeze dried to obtain 47.2 g of the product.

MS (ESI$^+$): (M+H)$^+$ 169/171
HPLC: RT=0.08/0.1 min, Method B

Intermediate 4.1

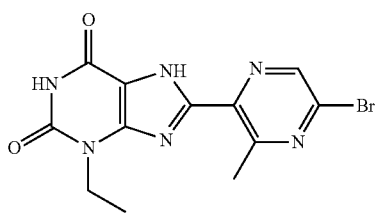

4.1.1

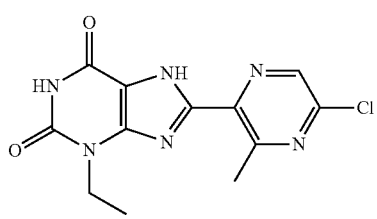

4.1.2

To a mixture of intermediate 3.2 (1.0 g, 4.8 mmol) in DMF (4.00 mL, 49.2 mmol) and DMSO (4.00 mL, 56.3 mmol) 5-bromo-3-methylpyrazine-2-carbaldehyde (973 mg, 4.8 mmol) was added and the mixture was stirred 45 min at 120° C. in the microwave. H$_2$O was added, the obtained precipitate was filtered and dried to obtain 0.97 g of the products (mixture of product 1/product 2 50/50).

MS (ESI$^+$): (M+H)$^+$ 351 intermediate 4.1.1
HPLC: RT=0.62 min, Method C
HPLC: RT=0.60 min, Method C intermediate 4.1.2

Intermediate 4.2

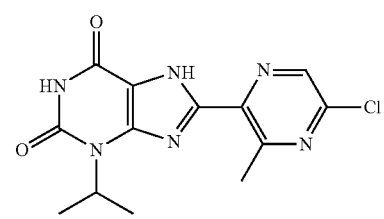

4.2

Intermediate 4.2 was prepared in an analogous manner to intermediate 4.1 using intermediate 3.1 and 5-bromo-3-methylpyrazine-2-carbaldehyde.

MS (ESI$^+$): (M+H)$^+$ 321
HPLC: RT=0.75 min, Method F

Intermediate 4.3

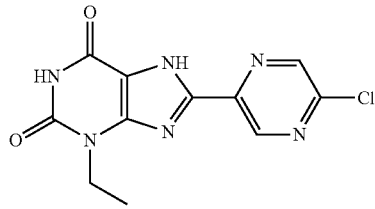
4.3

To a mixture of intermediate 3.2 (459 mg, 2.0 mmol) in THF (8 mL, 99.7 mmol) and DMSO (8 mL, 112.5 mmol) 5-chloropyrazine-2-carbaldehyde (342 mg, 2.4 mmol) was added and the mixture was stirred 45 min at 125° C. in the microwave. H$_2$O was added, the obtained precipitate was filtered and dried to obtain 403 mg of the product.

MS (ESI$^+$): (M+H)$^+$ 293

HPLC: RT=0.56 min, Method F

Intermediate 5.1

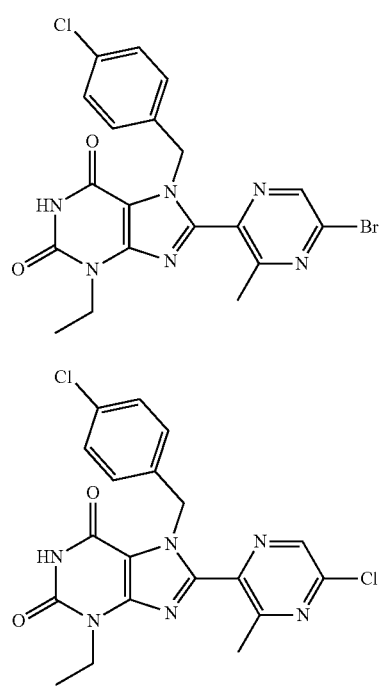
5.1.1

5.1.2

To a mixture of intermediate 4.1 (mix of 4.1.1/4.1.2 50/50, 0.3 g, 0.85 mmol) in DMF (2.0 mL), DIPEA (0.176 mL, 1.03 mmol) and 1-(bromomethyl)-4-chlorobenzene (176 mg, 0.85 mmol) were added and the mixture was stirred 2.5 h at 80° C. The reaction mixture was acidified and purified by chromatography to obtain 246 mg of the product (mixture of product 1/product 2 50/50).

MS (ESI$^+$): (M+H)$^+$ 477 intermediate 5.1.1

HPLC: RT=0.97 min, Method F

MS (ESI$^+$): (M+H)$^+$ 431 intermediate 5.1.2

HPLC: RT=0.95 min, Method F

Intermediate 5.2

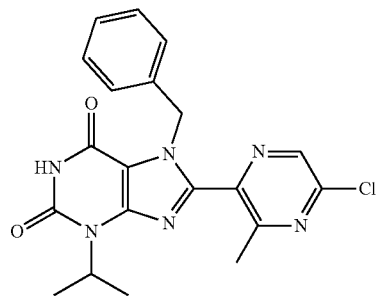
5.2

To a mixture of intermediate 4.2 (358 mg, 1.12 mmol) in DMF (2 mL), THF (1 mL) and DMSO (1 mL) DIPEA (0.230 mL, 1.34 mmol) and (bromomethyl)benzene (0.133 mL, 1.12 mmol) were added and the mixture was stirred 2.5 h at 80° C. The mixture was acidified with TFA and purified by chromatography to obtain 294 mg of the product.

MS (ESI$^+$): (M+H)$^+$ 411

HPLC: RT=0.96 min, Method F

Intermediate 5.3

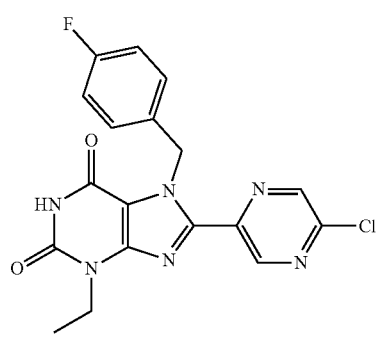
5.3

To a mixture of intermediate 4.3 (200 mg, 0.68 mmol) in DMF (7.88 mL, 96.9 mmol) and THF (7.77 mL, 96.9 mmol), K$_2$CO$_3$ (236 mg, 1.71 mmol) and 1-(bromomethyl)-4-fluorobenzene (70.4 µL, 0.57 mmol) were added and the mixture was stirred overnight at rt. The reaction mixture was diluted with ACN, filtered and purified by chromatography to obtain 81 mg of the product.

MS (ESI$^+$): (M+H)$^+$ 402

HPLC: RT=0.62 min, Method D

Intermediate 5.4

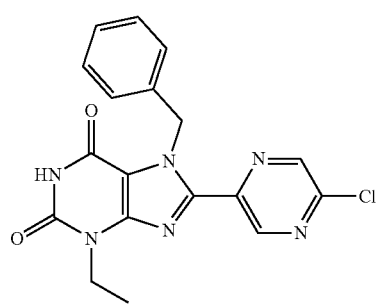
5.4

To a mixture of intermediate 4.3 (200 mg, 0.68 mmol) in DMF (7.88 mL) and THF (7.77 mL) K₂CO₃ (236 mg, 1.7 mmol) and (bromomethyl)benzene (67.8 μL, 0.57 mmol) were added and the mixture was stirred overnight at rt. The mixture was diluted with ACN (5 mL), filtered and purified by chromatography to obtain 90.0 mg of the product.

MS (ESI⁺): (M+H)⁺ 383
HPLC: RT=0.61 min, Method D

Intermediate 5.5

5.5.1

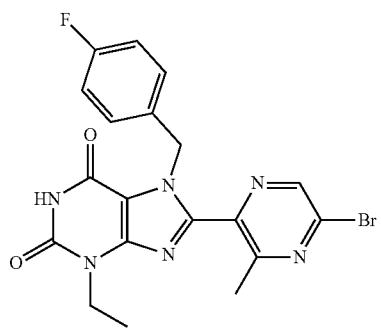

5.5.2

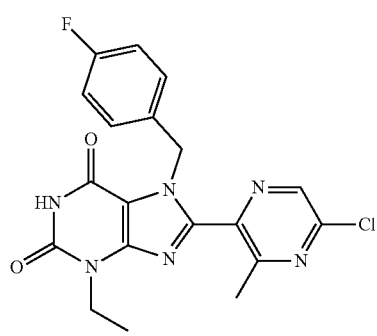

To a mixture of intermediate 4.1 (mix of 4.1.1/4.1.2 50/50, 200 mg, 0.57 mmol) in DMF (2.0 mL), DIPEA (118 μL, 0.683 mmol) and 1-(bromomethyl)-4-fluorobenzene (70.4 μL, 0.57 mmol) were added and the mixture was stirred 2.5 h at 80° C. The reaction mixture was acidified and purified by chromatography to obtain 136 mg of the product (mixture of product 1/product 2 50/50).

MS (ESI⁺): (M+H)⁺ 461 intermediate 5.5.1
HPLC: RT=0.91 min, Method F
MS (ESI⁺): (M+H)⁺ 415 intermediate 5.5.2
HPLC: RT=0.89 min, Method F Intermediate 5.6

5.6.1

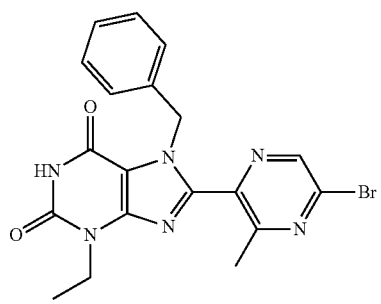

5.6.2

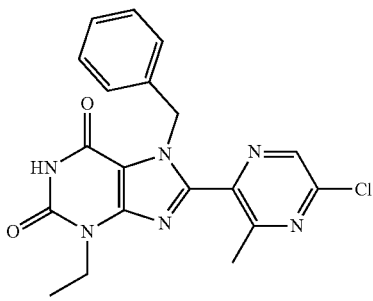

To a mixture of intermediate 4.1 (mix of 4.1.1/4.1.2 50/50, 466 mg, 1.326 mmol) in DMF (2.0 mL), DIPEA (274 μL, 1.592 mmol) and (bromomethyl)benzene (158 μL, 1.326 mmol) were added and the mixture was stirred 2.5 h at 80° C. The reaction mixture was acidified and purified by chromatography to obtain 508 mg of the product (mixture of product 1/product 2 50/50).

MS (ESI⁺): (M+H)⁺ 443 intermediate 5.6.1
HPLC: RT=0.88 min, Method F
MS (ESI⁺): (M+H)⁺ 397 intermediate 5.6.2
HPLC: RT=0.85 min, Method F Intermediate 6.1

6.1.1

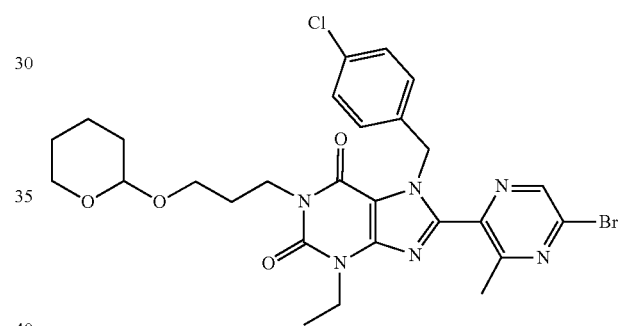

6.1.2

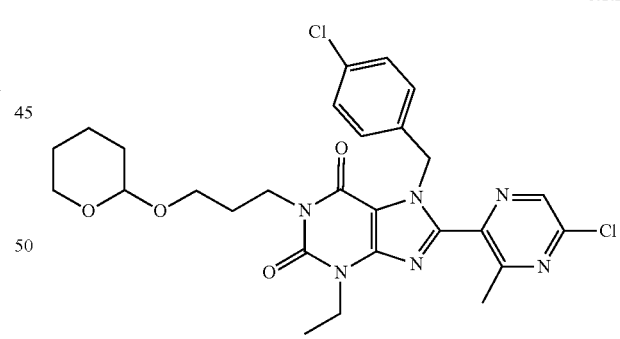

To a mixture of intermediate 5.1 (mixture of 5.1.1/5.1.2 50/50, 0.245 g, 0.515 mmol) in anhydrous DMF (3 mL) K₂CO₃ (0.142 g, 1.030 mmol) and 2-(3-bromopropoxy)oxane (0.131 mL, 0.773 mmol) were added and the mixture was stirred for 2 h at 80° C. H₂O was added and extracted with EtOAc. The combined organic layers were dried, concentrated in vacuo and the resulting crude product was purified by chromatography to obtain 269 mg of the product (mixture of 6.1.1/6.1.2 50/50).

MS (ESI⁺): (M+H)⁺ 617 intermediate 6.1.1
HPLC: RT=0.88 min, Method D
MS (ESI⁺): (M+H)⁺ 574 intermediate 6.1.2
HPLC: RT=0.87 min, Method D Intermediate 6.2

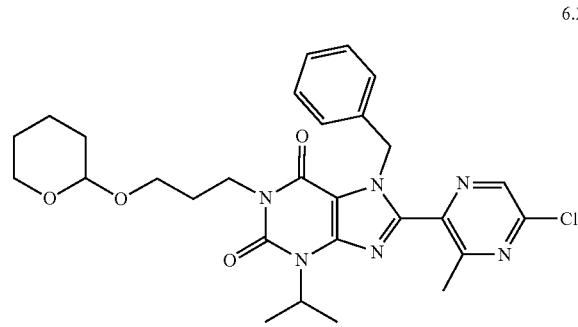 [SMILES: Cc1nc(Cl)cnc1-c1nc2c(c(=O)n(CCCOC3CCCCO3)c(=O)n2C(C)C)n1Cc1ccccc1]

Intermediate 6.2 was prepared in an analogous manner to intermediate 6.1 using intermediate 5.2 (1 h, 80° C.).

MS (ESI$^+$): (M+H)$^+$ 553

HPLC: RT=0.88 min, Method D

Intermediate 6.3

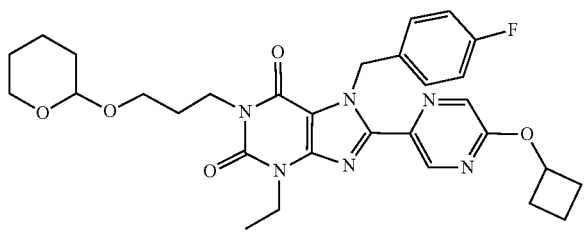

To a mixture of intermediate 7.3 (85 mg, 0.20 mmol) in THF (1.42 mL) and DMSO (1.2 mL) K$_2$CO$_3$ (80.8 mg, 0.58 mol) and 2-(3-bromopropoxy)oxane (49.6 µL, 0.29 mmol) were added and the mixture was stirred for 1 h at 90° C. The mixture was cooled and purified by chromatography to obtain 65.0 mg of the product.

MS (ESI$^+$): (M+H-THP)$^+$ 495

HPLC: RT=0.83 min, Method D

Intermediate 6.4

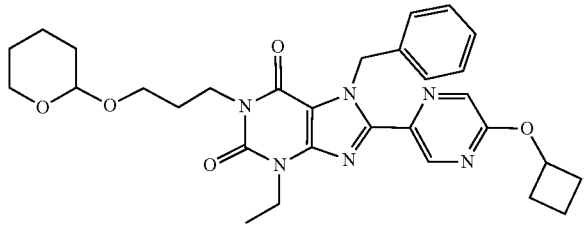

Intermediate 6.4 was prepared in an analogous manner to intermediate 6.3 using intermediate 7.4.

MS (ESI$^+$): (M+H-THP)$^+$ 477

HPLC: RT=0.82 min, Method D

Intermediate 6.5

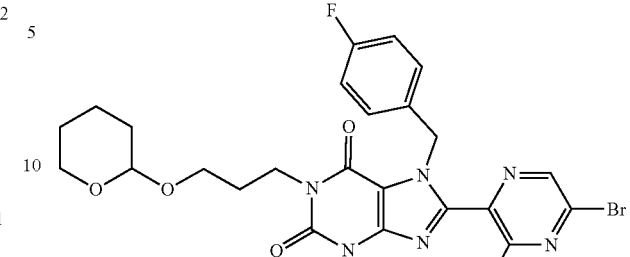

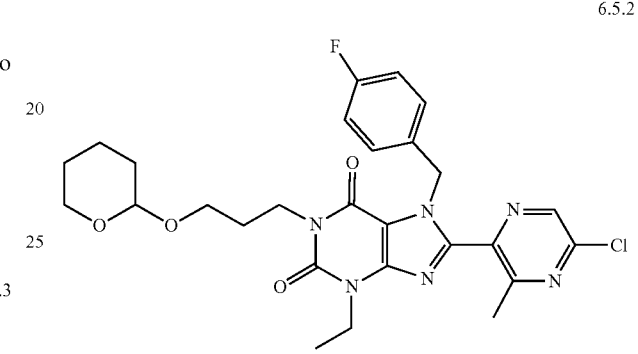

To a mixture of intermediate 5.5 (mixture of 5.5.1/5.5.2 50/50, 135 mg, 0.294 mmol) in anhydrous DMF (3 mL) K$_2$CO$_3$ (81.3 mg, 0.588 mmol) and 2-(3-bromopropoxy)oxane (75 µL, 0.441 mmol) were added and the mixture was stirred 2 h at 80° C. H$_2$O was added and extracted with EtOAc. The combined organic layers were dried, concentrated in vacuo, purified by chromatography and freeze dried to obtain 708 mg of the product (mixture of 6.5.1/6.5.2 50/50).

MS (ESI$^+$): (M+H)$^+$ 601 intermediate 6.5.1

HPLC: RT=0.83 min, Method D

MS (ESI$^+$): (M+H)$^+$ 558 intermediate 6.5.2

HPLC: RT=0.80 min, Method D

Intermediate 6.6

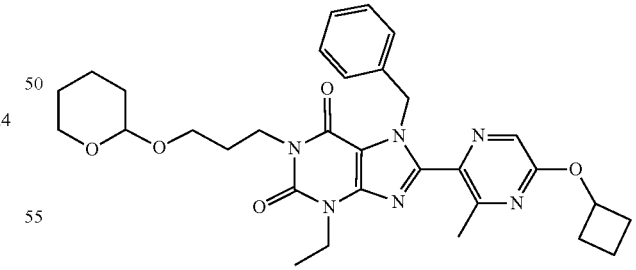

To a mixture of intermediate 7.6 (92 mg, 0.212 mmol) in anhydrous DMF (2 mL) K$_2$CO$_3$ (58.5 mg, 0.423 mmol) and 2-(3-bromopropoxy)oxane (53.8 µL, 0.317 mmol) were added and the mixture was stirred 2 h at 50° C. H$_2$O was added and extracted with EtOAc. The combined organic layers were dried and concentrated in vacuo to obtain crude product that was used without further purification.

MS (ESI$^+$): (M+H)$^+$ 575

HPLC: RT=1.29 min, Method F

Intermediate 7.1

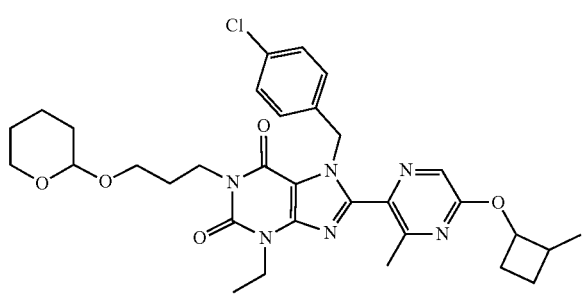

To a mixture of intermediate 6.1 (mixture of 6.1.1/6.1.2 50/50, 83 mg, 0.134 mmol) in dioxane (1.5 mL) 2-methyl-cyclobutan-1-ol (0.5 mL) and sodium hydride (55%, 11.7 mg, 0.269 mmol) were added. The mixture was stirred for 6 h at 100° C. H$_2$O was added and extracted with EtOAc. The combined organic layers were dried and concentrated in vacuo to obtain crude product that was used without further purification.

MS (ESI$^+$): (M+H)$^+$ 623

HPLC: RT=0.99 min, Method D

Intermediate 7.2

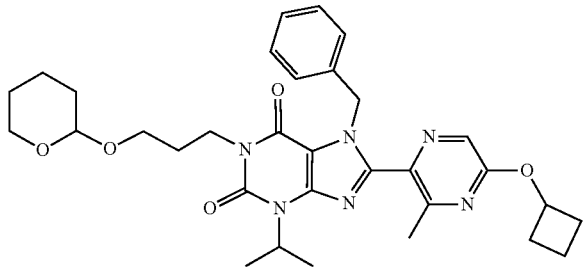

To a mixture of cyclobutanol (1 mL, 12.8 mmol) and sodium hydride (11.1 mg, 0.25 mmol) in DMF (1 mL) intermediate 6.2 (70 mg, 0.13 mmol) was added and the reaction was stirred 4.5 h at 110° C. H$_2$O was added and extracted with EtOAc. The combined organic layers were dried and concentrated in vacuo to obtain crude product that was used without further purification.

MS (ESI$^+$): (M+H)$^+$ 589

HPLC: RT=0.86 min, Method D

Intermediate 7.3

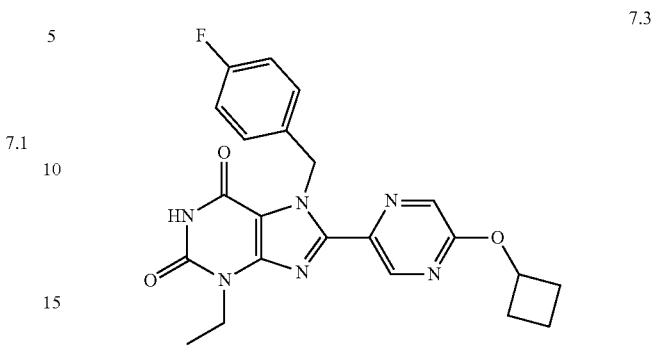

A mixture of intermediate 5.3 (81.0 mg, 0.20 mmol) and cyclobutanol (0.02 mL, 0.24 mmol) in THF (0.41 ml, 5.05 mmol) was cooled to 0°, then potassium 2-methylpropan-2-olate (45.4 mg, 0.40 mmol) was added and the reaction was stirred 6 h at reflux. The mixture was cooled, H$_2$O was added and the precipitate was filtered and dried to obtain 85.0 mg of the product.

MS (ESI$^+$): (M+H)$^+$ 437

HPLC: RT=0.69 min, Method D

Intermediate 7.4

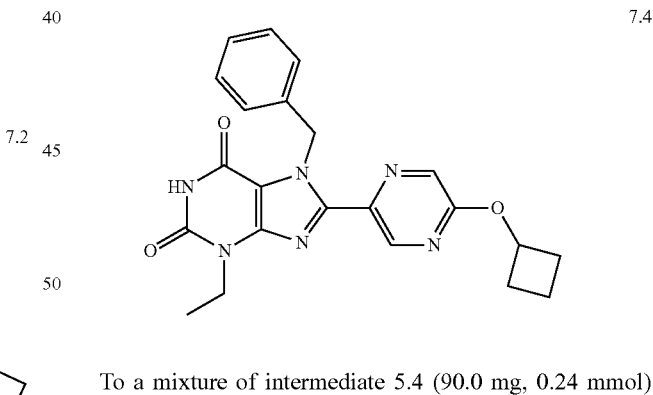

To a mixture of intermediate 5.4 (90.0 mg, 0.24 mmol) and cyclobutanol (0.02 mL, 0.28 mmol) in THF (0.47 ml) potassium 2-methylpropan-2-olate (52.8 mg, 0.47 mmol) was added under ice cooling and the reaction was stirred 30 min at rt. Additional potassium 2-methylpropan-2-olate and cyclobutanol were added and the mixture was stirred overnight at rt. Additional cyclobutanol and potassium 2-methylpropan-2-olate were added and the mixture was stirred 6 h at reflux. The mixture was cooled. H$_2$O was added and the precipitate was filtered and dried to obtain 93.0 mg of the product.

MS (ESI$^+$): (M+H)$^+$ 419

HPLC: RT=0.68 min, Method D

Intermediate 7.5

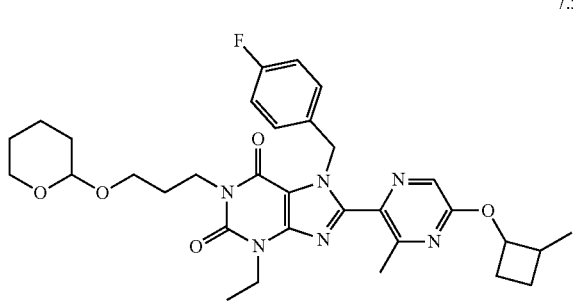

7.5

To a mixture of intermediate 6.5 (mixture of 6.5.1/6.5.2 50/50, 52 mg, 0.086 mmol) in dioxane (1.5 mL) 2-methyl-cyclobutan-1-ol (0.5 mL) and sodium hydride (55%, 7.6 mg, 0.173 mmol) were added. The mixture was stirred for 6 h at 100° C. H$_2$O was added and extracted with EtOAc. The combined organic layers were dried and concentrated in vacuo to obtain crude product that was used without further purification.

MS (ESI$^+$): (M+H)$^+$ 607

HPLC: RT=0.95 min, Method D

Intermediate 7.6

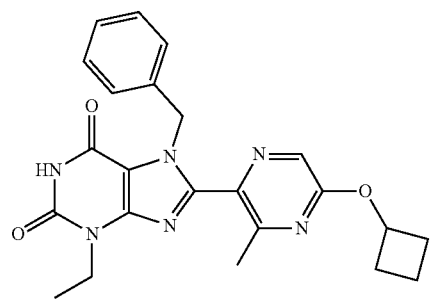

7.6

To a mixture of intermediate 5.6 (mixture of 5.6.1/5.6.2 50/50, 100 mg, 0.227 mmol) in dioxane (1.0 mL) cyclobutanol (2.0 mL) and sodium hydride (55%, 19.8 mg, 0.453 mmol) were added. The mixture was stirred 1.5 h at 100° C. H$_2$O was added and extracted with EtOAc. The combined organic layers were dried and concentrated in vacuo. The crude product was purified by chromatography to obtain 92.0 mg of the product.

MS (ESI$^+$): (M+H)$^+$ 433

HPLC: RT=1.03 min, Method F

EXAMPLES

Example 1

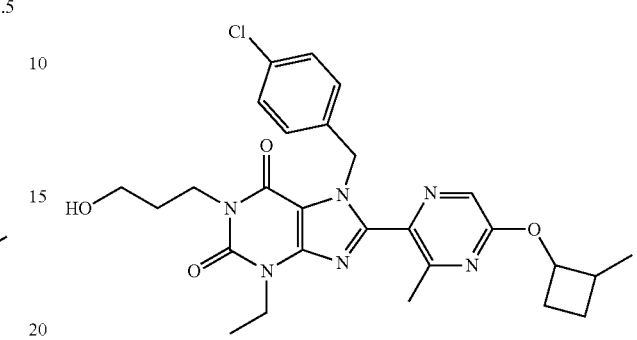

1

To a mixture of intermediate 7.1 (83.0 mg, 0.133 mmol) in MeOH (1.0 mL) and THF (1.0 mL) toluene-4-sulfonic acid hydrate (31.7 mg, 0.166 mmol) was added. The mixture was stirred for 1.5 h at rt. The mixture was concentrated in vacuo and purified by chromatography to obtain 2.1 mg of the product.

MS (ESI$^+$): (M+H)$^+$ 540/542 (Cl isotope pattern)

HPLC: RT=1.2 min, Method F

Example 2

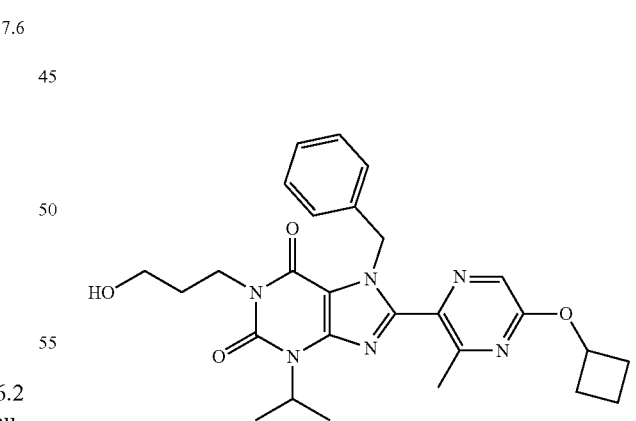

2

To a mixture of intermediate 7.2 (74.0 mg, 0.13 mmol) in MeOH (1.0 mL) and THF (1.0 mL) toluene-4-sulfonic acid hydrate (30 mg, 0.16 mmol) was added. The mixture was stirred 1 h at rt. The mixture was purified by chromatography to obtain 55.0 mg of the product.

MS (ESI$^+$): (M+H)$^+$ 506

HPLC: RT=0.75 min, Method D

Example 3

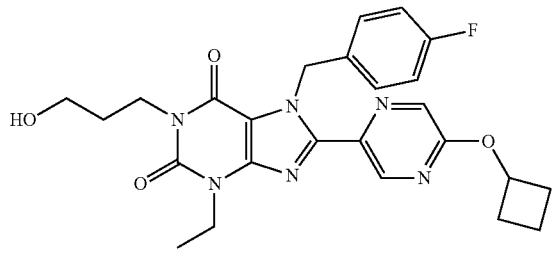

To a mixture of intermediate 6.3 (65.0 mg, 0.11 mmol) in MeOH (1.0 mL) toluene-4-sulfonic acid hydrate (107 mg, 0.56 mmol) was added. The mixture was stirred 30 min at rt. The mixture was purified by chromatography to obtain 45.0 mg of the product.
MS (ESI$^+$): (M+H)$^+$ 496
RT=0.71 min, Method D Example 4

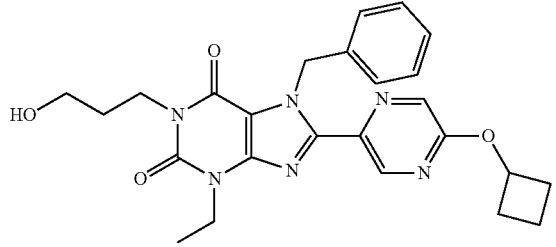

Example 4 was prepared in an analogous manner to example 3 using intermediate 6.4.
MS (ESI$^+$): (M+H)$^+$ 478
RT=0.70 min, Method D Example 5

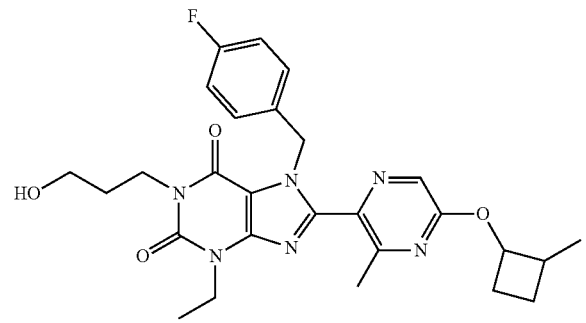

To a mixture of intermediate 7.5 (52.0 mg, 0.086 mmol) in MeOH (1 mL) and THF (1 mL) toluene-4-sulfonic acid hydrate (20.4 mg, 0.107 mmol) was added and the mixture was stirred 1.5 h at rt. The mixture was purified by chromatography to obtain 8.6 mg of the product.
MS (ESI$^+$): (M+H)$^+$ 524
RT=1.14 min, Method F Example 6

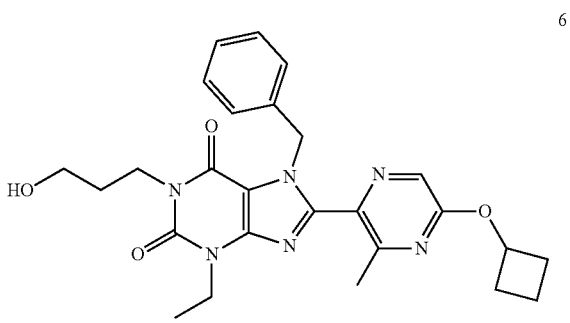 [SMILES: CCn1c(=O)n(CCCO)c(=O)c2c1nc(-c1ncc(OC3CCC3)nc1C)n2Cc1ccccc1]

Example 6 was prepared in an analogous manner to example 5 using intermediate 6.6.
MS (ESI$^+$): (M+H)$^+$ 492
RT=0.77 min, Method D
1H NMR (DMSO-d6) δ 8.21 (s, 1H), 7.16-7.24 (m, 3H), 6.94-6.96 (m, 2H), 6.81, 5.71 (s, 2H), 5.19 (sept, J=7.2 Hz, 1H), 4.42 (t, J=5.3 Hz, 1H), 4.08 (q, J=7.1 Hz, 2H), 3.96 (dd, J=8.0, 6.7 Hz, 2H), 3.43-3.48 (m, 2H), 2.39-2.47 (m, 2H), 2.34 (s, 3H), 2.05-2.18 (m, 2H), 1.61-1.85 (m, 4H), 1.27 (d, J=7.0 Hz, 3H).

The invention claimed is:
1. A compound of formula I:

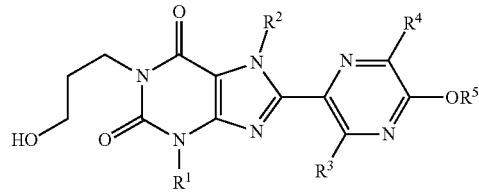

or a stereoisomer thereof,
wherein:
R$^1$ is CH$_2$CH$_3$, CH(CH$_3$)$_2$, CH$_2$CH(CH$_3$)$_2$, or cyclobutyl;
R$^2$ is:

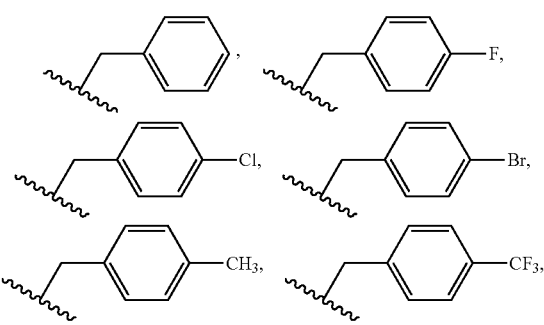

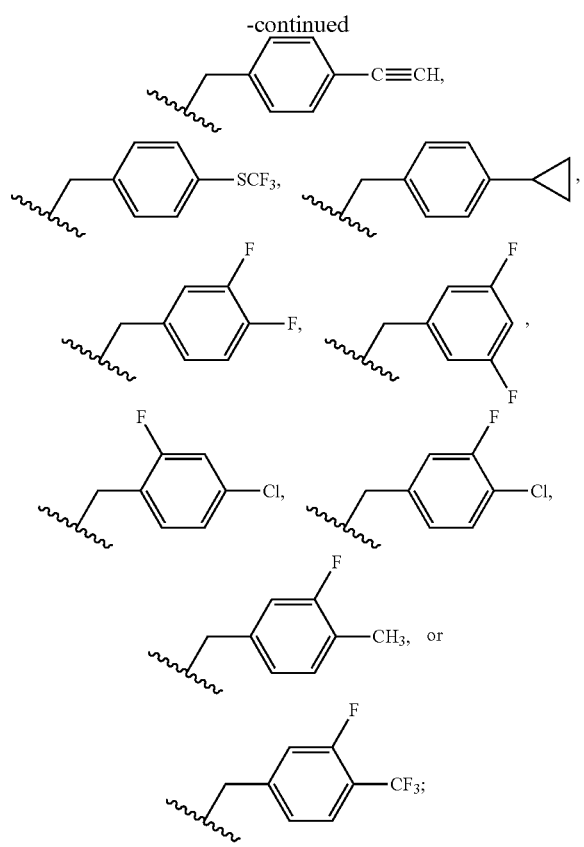

R³ is H, F, or C₁-C₃ alkyl, wherein the C₁-C₃ alkyl is optionally substituted with one or more F substituents;
R⁴ is H or F; and
R⁵ is:

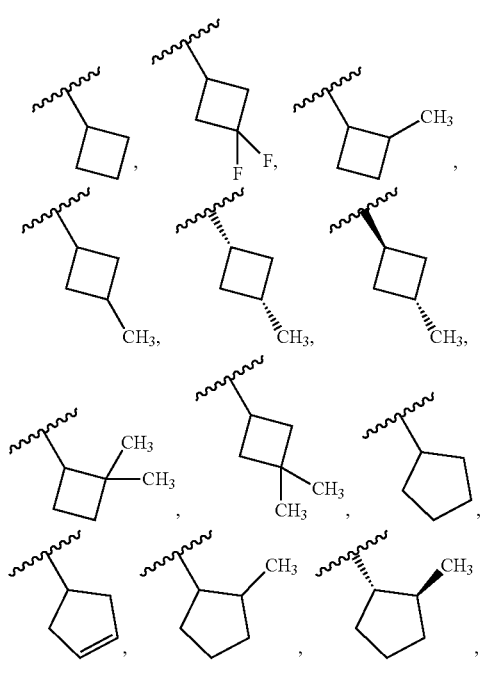

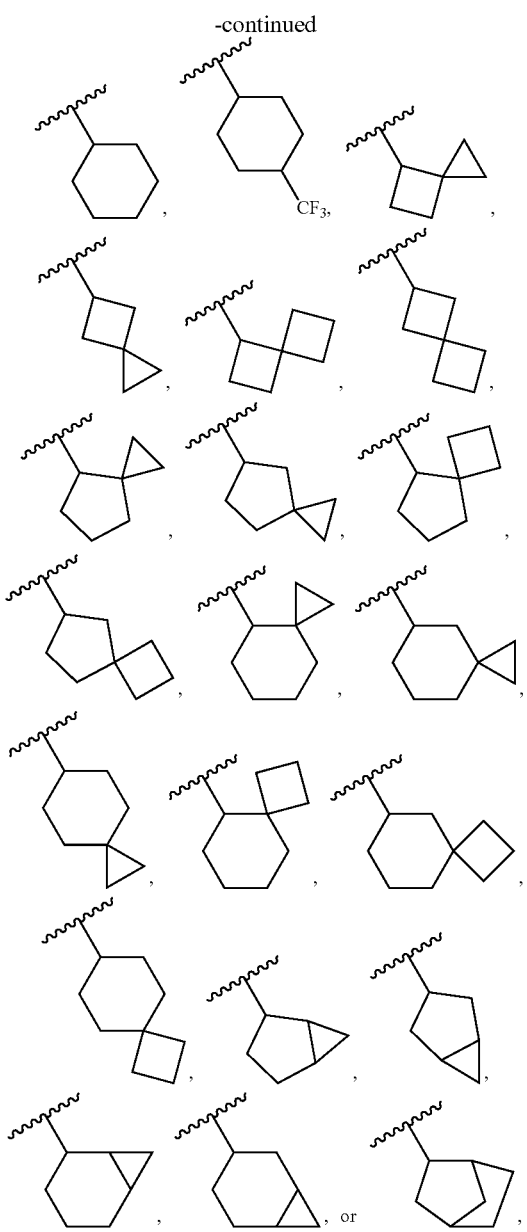

wherein R⁵ is further optionally substituted with any one of (a), (b), or (c):
(a) one or more F substituents; or
(b) one or more C₁-C₃ fluoroalkyl substituents; or
(c) one or more F substituents and one or more C₁-C₃ fluoroalkyl substituents.

2. The compound according to claim 1, or a stereoisomer thereof, wherein:
R¹ is CH₂CH₃, CH(CH₃)₂, or CH₂CH(CH₃)₂;
R² is:

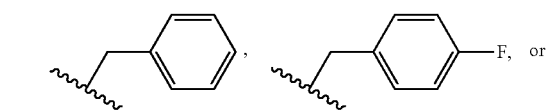

-continued

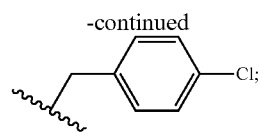

R³ is H or CH₃;
R⁴ is H; and
R⁵ is:

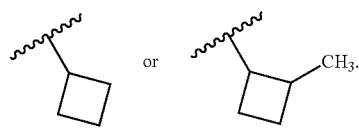 [SMILES: *C1CCC1 ; "or" ; *C1CCC1C]

3. The compound according to claim 1, wherein the compound is selected from the group consisting of:

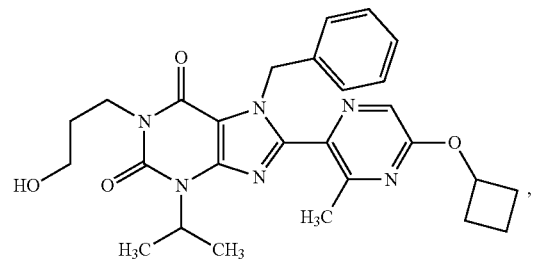

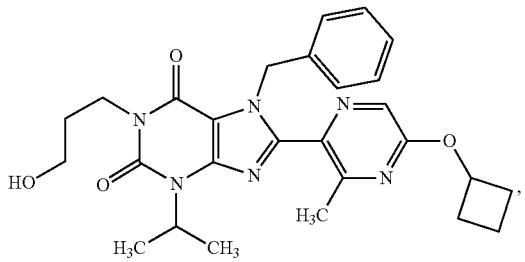

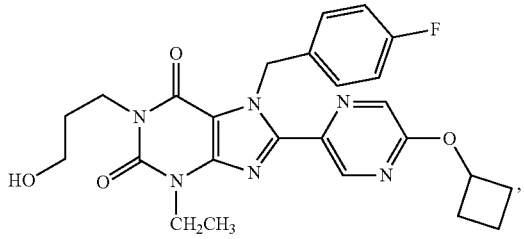

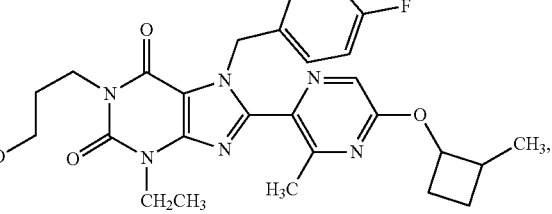

and

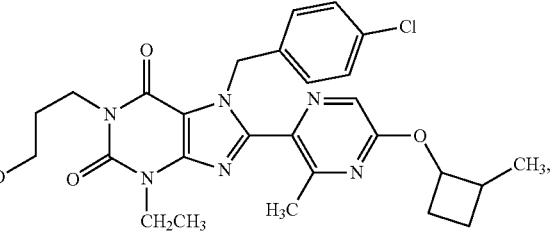

or a stereoisomer thereof.

4. A pharmaceutical composition comprising a pharmaceutically acceptable carrier or excipient and the compound according to claim 1, or a stereoisomer thereof.

5. The pharmaceutical composition according to claim 4, wherein the compound is selected from the group consisting of:

or a stereoisomer thereof.

6. A method for inhibiting a transient receptor potential cation channel subfamily C, member 5 (TRPC5) mediated current in a cell, wherein the method comprises contacting the cell with an effective amount of the compound according to claim 1, or a stereoisomer thereof.

7. A method for inhibiting a transient receptor potential cation channel subfamily C, member 5 (TRPC5) mediated current in a subject, wherein the method comprises administering to the subject in need thereof a therapeutically effective amount of the compound according to claim 1, or a stereoisomer thereof.

8. The method according to claim 7, wherein the subject has a transient receptor potential cation channel subfamily C, member 5 (TRPC5) mediated condition or disorder selected from the group consisting of a neurodegenerative condition, a neurodegenerative disorder, a neurological condition, a neurological disorder, a psychiatric condition, and a psychiatric disorder.

9. The method according to claim 8, wherein the neurodegenerative condition, the neurodegenerative disorder, the neurological condition, the neurological disorder, the psychiatric condition, or the psychiatric disorder is selected from the group consisting of Alzheimer's disease, amyotrophic lateral sclerosis, anxiety, a brain disorder caused by aging, a brain disorder caused by trauma, a disorder associated with addiction, a disorder associated with dysregulated emotional processing, a disorder associated with impaired impulse control, a fear-related disorder, Huntington's disease, a memory disorder, Parkinson's disease, and pain.

10. The method according to claim 9, wherein the disorder associated with dysregulated emotional processing is borderline personality disorder or a depressive disorder.

11. The method according to claim 10, wherein the depressive disorder is selected from the group consisting of bipolar disorder, dysthymia, major depression, major depressive disorder, postpartum depression, and psychiatric depression.

12. The method according to claim 9, wherein the fear-related disorder is selected from the group consisting of agoraphobia, generalized anxiety disorder, obsessive compulsive disorder, panic disorder, post-traumatic stress disorder, separation anxiety, social anxiety disorder, and a social phobia.

13. The method according to claim 9, wherein the memory disorder is selected from the group consisting of Alzheimer's disease, amnesia, aphasia, a brain injury, a brain tumor, chronic fatigue syndrome, Creutzfeldt-Jakob disease, dissociative amnesia, fugue amnesia, Huntington's disease, a learning disorder, multiple personality disorder, post-traumatic stress disorder, schizophrenia, a sleep disorder, a sports injury, a stroke, and Wernicke-Korsakoff syndrome.

14. A pharmaceutically acceptable salt of a compound of formula I:

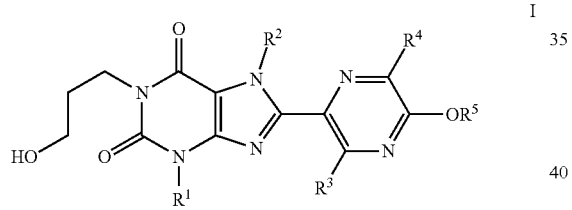

or a stereoisomer thereof,
wherein:
$R^1$ is $CH_2CH_3$, $CH(CH_3)_2$, $CH_2CH(CH_3)_2$, or cyclobutyl;
$R^2$ is:

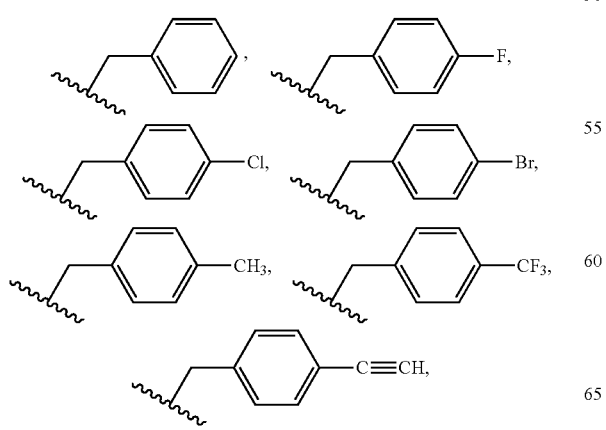

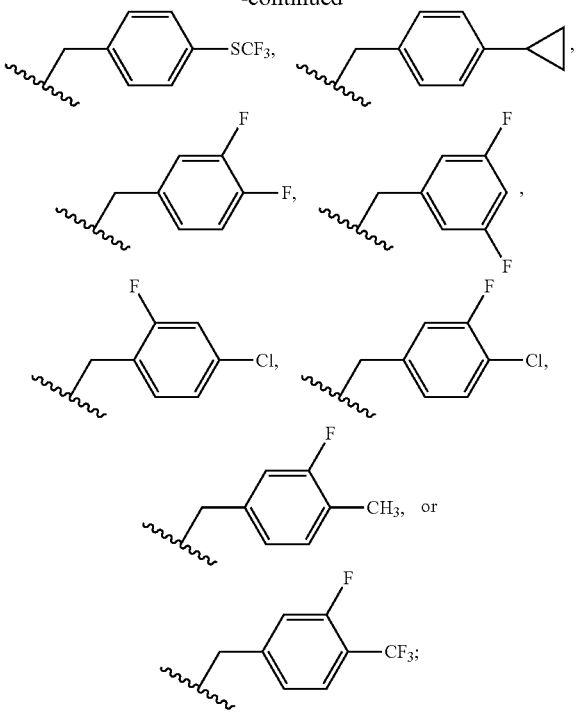

$R^3$ is H, F, or $C_1$-$C_3$ alkyl, wherein the $C_1$-$C_3$ alkyl is optionally substituted with one or more F substituents;
$R^4$ is H or F; and
$R^5$ is:

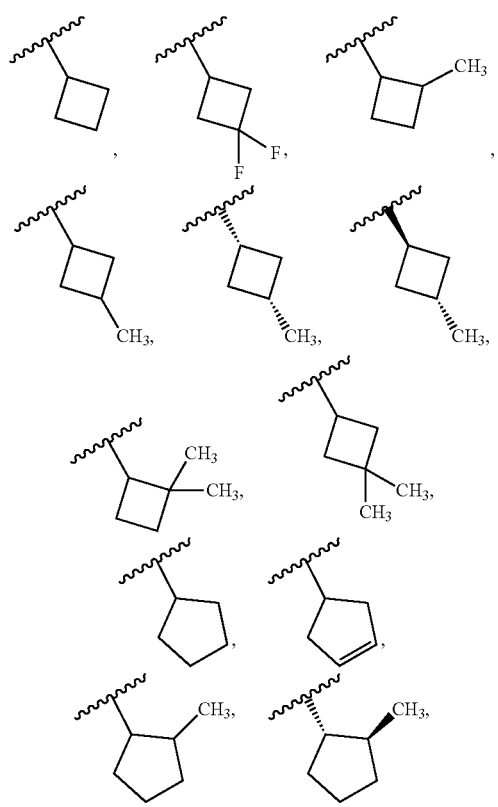

-continued

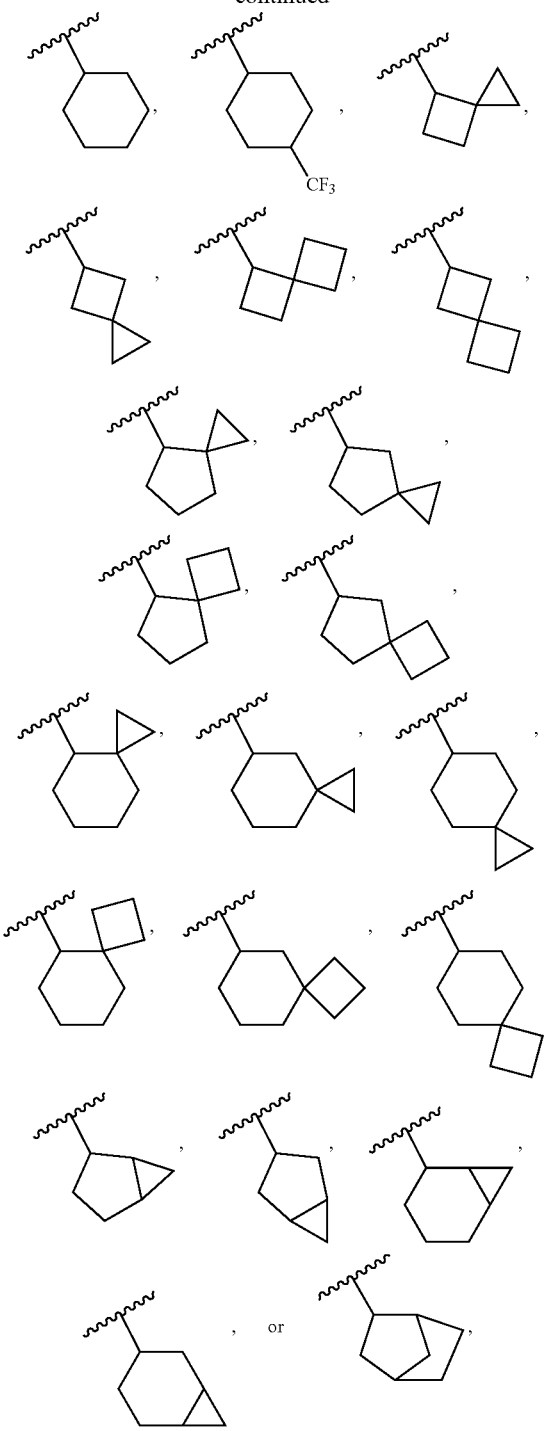

wherein R⁵ is further optionally substituted with any one of (a), (b), or (c):
(a) one or more F substituents; or
(b) one or more $C_1$-$C_3$ fluoroalkyl substituents; or
(c) one or more F substituents and one or more $C_1$-$C_3$ fluoroalkyl substituents.

15. The pharmaceutically acceptable salt of the compound according to claim 14, wherein the compound is selected from the group consisting of:

or a stereoisomer thereof.

16. A pharmaceutical composition comprising a pharmaceutically acceptable carrier or excipient and the pharmaceutically acceptable salt of the compound according to claim 14, or a stereoisomer thereof.

17. The pharmaceutical composition according to claim 16, wherein the compound is selected from the group consisting of:

-continued

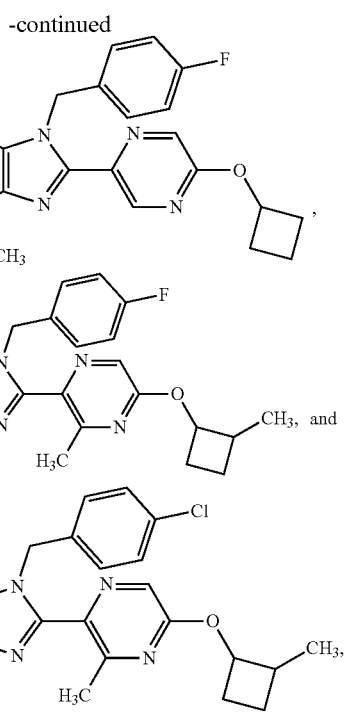

or a stereoisomer thereof.

18. A method for inhibiting a transient receptor potential cation channel subfamily C, member 5 (TRPC5) mediated current in a cell, wherein the method comprises contacting the cell with an effective amount of the pharmaceutically acceptable salt of the compound according to claim 14, or a stereoisomer thereof.

19. A method for inhibiting a transient receptor potential cation channel subfamily C, member 5 (TRPC5) mediated current in a subject, wherein the method comprises administering to the subject in need thereof a therapeutically effective amount of the pharmaceutically acceptable salt of the compound according to claim 14, or a stereoisomer thereof.

20. The method according to claim 19, wherein the subject has a transient receptor potential cation channel subfamily C, member 5 (TRPC5) mediated condition or disorder selected from the group consisting of a neurodegenerative condition, a neurodegenerative disorder, a neurological condition, a neurological disorder, a psychiatric condition, and a psychiatric disorder.

21. The method according to claim 20, wherein the neurodegenerative condition, the neurodegenerative disorder, the neurological condition, the neurological disorder, the psychiatric condition, or the psychiatric disorder is selected from the group consisting of Alzheimer's disease, amyotrophic lateral sclerosis, anxiety, a brain disorder caused by aging, a brain disorder caused by trauma, a disorder associated with addiction, a disorder associated with dysregulated emotional processing, a disorder associated with impaired impulse control, a fear-related disorder, Huntington's disease, a memory disorder, Parkinson's disease, and pain.

22. The method according to claim 21, wherein the disorder associated with dysregulated emotional processing is borderline personality disorder or a depressive disorder.

23. The method according to claim 22, wherein the depressive disorder is selected from the group consisting of bipolar disorder, dysthymia, major depression, major depressive disorder, postpartum depression, and psychiatric depression.

24. The method according to claim 21, wherein the fear-related disorder is selected from the group consisting of agoraphobia, generalized anxiety disorder, obsessive compulsive disorder, panic disorder, post-traumatic stress disorder, separation anxiety, social anxiety disorder, and a social phobia.

25. The method according to claim 21, wherein the memory disorder is selected from the group consisting of Alzheimer's disease, amnesia, aphasia, a brain injury, a brain tumor, chronic fatigue syndrome, Creutzfeldt-Jakob disease, dissociative amnesia, fugue amnesia, Huntington's disease, a learning disorder, multiple personality disorder, post-traumatic stress disorder, schizophrenia, a sleep disorder, a sports injury, a stroke, and Wernicke-Korsakoff syndrome.

* * * * *

UNITED STATES PATENT AND TRADEMARK OFFICE
CERTIFICATE OF CORRECTION

PATENT NO. : 12,291,532 B2  
APPLICATION NO. : 17/312831  
DATED : May 6, 2025  
INVENTOR(S) : Kai Gerlach Page 1 of 2

It is certified that error appears in the above-identified patent and that said Letters Patent is hereby corrected as shown below:

In the Claims

In Claim 3, at Column 37, Line 22, insert -- 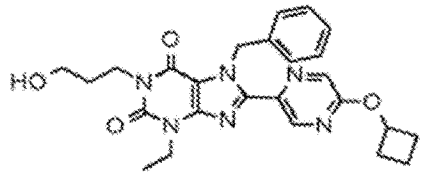 , 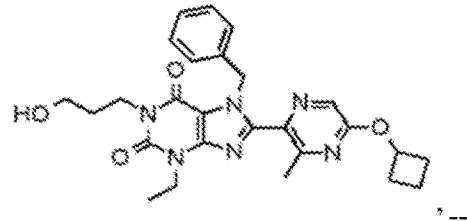 , --

In Claim 5, at Column 38, Line 1, insert -- 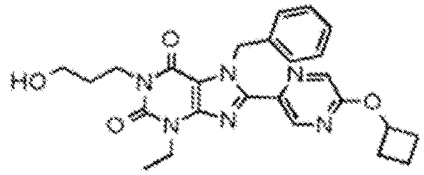 , 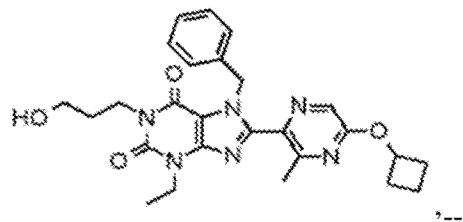 , --

Signed and Sealed this  
Thirtieth Day of September, 2025

John A. Squires  
*Director of the United States Patent and Trademark Office*

CERTIFICATE OF CORRECTION (continued)

In Claim 15, at Column 42, Line 1, insert -- 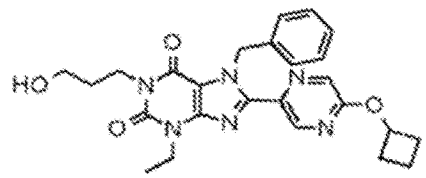 , 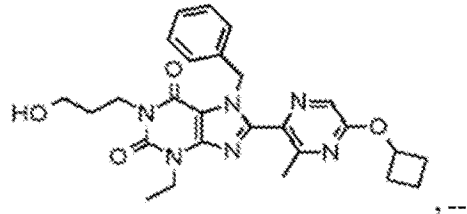 , --

In Claim 17, at Column 42, Line 55, insert -- 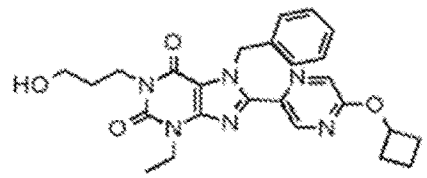 , 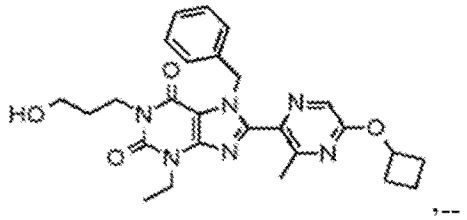 , --